(12) United States Patent
Miller et al.

(10) Patent No.: US 6,420,131 B1
(45) Date of Patent: Jul. 16, 2002

(54) USE OF FLUORESCEIN ARYL ETHERS IN HIGH THROUGHPUT CYTOCHROME P450 INHIBITION ASSAYS

(75) Inventors: Vaughn P. Miller, Arlington; David Streser, Natick; Charles L. Crespi, Marblehead, all of MA (US)

(73) Assignee: Gentest Corporation, Woburn, MA (US)

( * ) Notice: Subject to any disclaimer, the term of this patent is extended or adjusted under 35 U.S.C. 154(b) by 0 days.

(21) Appl. No.: 09/636,332

(22) Filed: Aug. 10, 2000

Related U.S. Application Data

(60) Provisional application No. 60/149,762, filed on Aug. 19, 1999, and provisional application No. 60/150,044, filed on Aug. 20, 1999.

(51) Int. Cl.⁷ .............................. C12Q 1/26; C12N 9/02; C12N 9/06
(52) U.S. Cl. .............................. 435/25; 549/391; 435/4; 435/6; 435/7.4; 435/189; 435/191; 435/968
(58) Field of Search ........................... 549/391; 435/25, 435/189, 4, 6, 7.4, 191, 968

(56) References Cited

U.S. PATENT DOCUMENTS

| | | | |
|---|---|---|---|
| 4,490,303 A | 12/1984 | Dean et al. | 260/453.99 |
| 5,055,595 A | 10/1991 | Wietfeld | 549/224 |
| 5,196,297 A | 3/1993 | Dumbrowski et al. | 430/338 |
| 5,576,424 A | 11/1996 | Mao et al. | 536/17.9 |
| 6,207,404 B1 * | 3/2001 | Miller et al. | 435/25 |

FOREIGN PATENT DOCUMENTS

| | | |
|---|---|---|
| EP | 0 353 953 | 2/1990 |
| WO | WO 87 03541 | 6/1987 |
| WO | WO 94 05688 | 3/1994 |
| WO | WO 97 39064 | 10/1997 |
| WO | WO 99 58710 | 11/1999 |
| WO | WO 00 04008 | 1/2000 |
| WO | WO 00 35900 | 6/2000 |

OTHER PUBLICATIONS

Computer CA Abstract 120:148476 Shen et al "Photoinduced Interactions Between Antracene Dyes and Onors/Acceptor" Gaojisu Tongxun (1991) 1 (7) 12–17.*
Computer CA Abstract 127:183143 He et al "A Photophysical Study on Antraquinone–Fluorescein–Anthracene" Dyes PIGM. (1997) 34 (3) 219–226.*

Miller, A.G, "Ethylated Fluoresceins: Assay of Cytochrome P–450 Activity and Application to Measurements in Single Cells by Flow Cytometry," *Analytical Biochemistry 133*, (1983), pp. 46–57.

White, I.N.H., et al., "Fluorescence–Activated Sorting of Rat Hepatocytes Based on their Mixed Function Oxidase Activities Towards Diethoxyfluorescein," *Biochem. J.*, 247 (1987), pp. 23–28.

Tadic, D et al., "Chiral Prodyes, Ethers and Esters of Dihydrofluorescein, Part 1: Dibenzyldihydrofluorescein (DBDF) a New Reagent," *Heterocycles*, vol. 31, #11, (1990), pp. 1975–1982.

Hargreaves, JS et al., "Photon Harvesting Polymers: Intracoil Energy Transfer in Anthryl– and Fluorescein–Tagged Polystyrene," *Can. J. Chem.*, 63 (1985), 1320–1327.

Mace, et al., "Development of CYP450–expressing human bronchial epithelial cell lines for in vitro pharmacotoxicologic applications" In Vitro toxicology, US, Mary Ann Liebert, New York, NY, vol. 10, No. 1, Mar. 21, 1997.

Haasch ML et al., "Use of 7–Aloxyphenoxazones, 7–Alkoxycoumarins and 7–Alkoxyquinolines as Lurorescent Substrates for Rainbow Trout Hepatic Microsomes After Treatment with Various Induces," Biochemical Pharmacology, GB, Pergamon, Oxford, vol. 47, No. 5, Mar. 2, 1994, pp. 893–903.

Tran, J., "Intramolecular triplet–triplet energy transfer from xanthene dyes to an anthryl substituent" *Journal of Photochemistry and Photobiology*, A: Chemistry., vol. 71, No. 1, 1993, pp. 45–49.

Amat–Guerri F., "Synthesis and spectroscopic propereties of new Rose Bengal and Eosin Y derivatives" Dyes and Pigments., vol. 12, No. 4, 1990, pp. 249–272.

He J., "Mechanism of primary photochemical reaction of eosin bis (diphenyliodonium) salt" *Chinese Science Bulletin.*, vol. 41, No. 1, 1996, pp. 38–43.

* cited by examiner

Primary Examiner—Herbert J. Lilling
(74) Attorney, Agent, or Firm—Wolf, Greenfield & Sacks, P.C.

(57) ABSTRACT

Novel fluorescent substrates of human cytochrome P450 enzymes are provided. Also provided are methods for their manufacture and use. These substrates are useful in assessing cytochrome P450 enzyme activity and in selecting compounds which inhibit cytochrome P450 enzyme activity and, in particular, for identifying potential adverse drug interactions which are mediated by inhibition of cytochrome P450 enzyme activity.

5 Claims, 5 Drawing Sheets

USE OF FLUORESCEIN ARYL ETHERS IN HIGH THROUGHPUT CYTOCHROME P450 INHIBITION ASSAYS

RELATED APPLICATIONS

This application claims priority under Title 35, U.S.C., §119(e), of U.S. Provisional Application No. 60/149,762, filed Aug. 19, 1999, and Provisional Application No. 60/150,044, filed Aug. 20, 1999, the entire contents of which are incorporated herein by reference.

FIELD OF INVENTION

This invention relates to the field of drug and xenobiotic metabolism. The invention includes novel cytochrome P450 fluorescent probe substrates and reaction products, methods for their preparation and their use as assay reagents.

BACKGROUND OF THE INVENTION

Cytochromes P450 (CYP) are the principal enzymes for the oxidative metabolism of many drugs, procarcinogens, promutagens, and environmental pollutants. Cytochrome P450 is a heme-containing, membrane-bound, multienzyme system that is present in many tissues in vivo but is present at the highest level in liver. In human liver, it is estimated that there are 15–20 different xenobiotic-metabolizing cytochrome P450 forms. A standard nomenclature based on relatedness of amino acid sequences has been developed. A relatively limited subset of these enzymes, CYP1A2, CYP2C8, CYP2C9, CYP2C19, CYP2D6 and CYP3A4 appear to be most commonly responsible for the metabolism of drugs and associated drug-drug interactions (*Spatzenegger and Jaeger*, 1995). The relative importance of this subset of enzymes is due to: the mass abundance of these enzymes (e.g. CYP3A4 is the most abundant P450 in human liver at ~30% of total P450), the preference of these enzymes to bind and/or metabolize chemical structures commonly found in drugs (e.g. CYP2D6 preferentially binds and metabolizes drugs with basic amine functionalities), enzyme polymorphisms (such as CYP3A4 and CYP2C19), and enzyme regulation in response to environmental chemicals some (such as CYP1A2 and CYP3A4). Competition for metabolism by a particular cytochrome P450 form is a principal mechanism of some clinically significant drug-drug interactions.

Identification of the enzymes responsible for metabolism is becoming an important aspect of drug development. Such identifications consider both the metabolism of the new drug as well as inhibition by the new drug. The identification of enzymes involved in metabolism of the new drug allows prediction, based on knowledge of the ability of coadministered drugs to inhibit the same enzymes, of which coadministered drugs may inhibit the metabolism of the new drug. This information can also be used to predict individual variability based on known metabolic polymorphisms. The identification of the enzymes most sensitive to inhibition by the new drug allows prediction, based on knowledge of which coadministered drugs are metabolized by the same enzyme, of which coadministered drug's metabolism may be inhibited by the new drug. Obtaining information for a series of drug candidates early in the drug discovery process can assist in the choice of the best drug candidate for further development.

Most cytochrome P450 assays have focused on the metabolism of drug molecules or drug candidates. While these chemicals are effective in assessing cytochrome P450 activity and inhibition, they are not amenable to high throughput screening assay technology (they require time consuming separation of enzyme reaction products using HPLC). Also, most of these substrates do not have the necessary fluorescent properties that make the substrate useful for in situ fluorescent plate analysis.

Sensitive fluorescent assays have been developed for human CYP1A1 and CYP1A2 enzymes. Members of the CYP1A family preferentially oxidize planar aromatic molecules not unlike the structure of common fluorescent chromophores. Microtiter plate based assays have been developed based on the O-dealkylation of alkyl ethers of resorufin (Donato, M. T. et. al., Anal. Biochem. 213, 29–33 (1993); Kennedy, S. W. and S. P. Jones, Anal. Biochem., 222, 217–223 (1994)) and coumarin (C. L. Crespi et al. Anal Biochem. 248, 188–190, (1997)). An intact cell assay using an alkyl ether of fluorescein (Quan, T. et al., Carcinogenesis 15, 1827–32, (1994)) has been described.

The development of fluorescent assays for other cytochromes P450 has been more challenging. We have described microtiter plate based assays for CYP2D6 based on alkylcoumarin derivatives (C. L. Crespi et al. Anal Biochem. 248, 188–190, (1997); Miller, V. P. and C. L. Crespi, U.S. patent application Ser. No. 09/352,576, entitled "Novel CYP2D Fluorescent Assay Reagents," filed Jul. 12, 1999.) We have also reported the use of commercial alkylcoumarins for the fluorescent assay of CYP2C9 and CYP2C19. However, the sensitivity (signal to noise ratio) of these CYP2C assays is limited. New substrates which increase the assay signal and minimize the required amount of enzyme reagent would be useful. No fluorescent substrate has been reported for the important drug metabolizing enzyme CYP2C8. CYP2C8 is the primary cytochrome P450 enzyme responsible for the metabolism of the anticancer drug paclitaxel (TAXOL™).

Among the different cytochromes P450 expressed in the liver, CYP3A4 is the most abundant. Important classes of substrates for this enzyme include steroids, macrolide antibiotics, antivirals, and polycyclic aromatic hydrocarbons. As the majority of commercially available drugs are metabolized by CYP3A4, the importance of screening for inhibition of this enzyme is essential in drug development. We have previously reported the use of the commercially available 7-benzyloxyresorufin (BzRes) as a fluorescent substrate for assessing CYP3A4 activity in a high throughput mode (Crespi et al. Anal Biochem. 248, 188–190, (1997)). We and others have demonstrated that the inhibition potential (e.g. $IC_{50}$ value) or activation potential for most compounds varies dramatically depending on the probe substrate used (K E Thummel and G R Wilkinson, Ann. Rev. Pharmacol. Toxicol. 38:389–430 (1998)). Additional fluorescent probe substrates, which differ significantly in structure and chemical properties from the current substrates, are needed to gain a better understanding of the potential for test compounds to inhibit CYP3A4.

Fluorescein ethers have been reported to be useful fluorescent cytochrome P450 assay reagents. A. G. Miller (A. G. Miller, Anal. Biochem. 133, 46–57 (1983)) described a series of ethylated fluoresceins. Ethoxyfluorescein ethyl ether, reportedly was the most useful for the flow cytometric analysis and sorting of intact, viable rat cells based on cytochrome P450 activity. Other laboratories have also reported using the diethoxy- or a dimethoxyflourescein derivative for the same purpose with rat or porcine cells (White et al., Biochem. J. 247, 23–28 (1987); Pan et al, Artif. Organs 20, 1173–1180 (1996); Anderson et al., Int. J. Artif. Organs 21, 360–364, (1998)). More recently, ethoxyfluorescein ethyl ester has been reported to monitor the activity of human skin fibroblasts transfected with human CYP1A1 cDNA (Quan, T. et al., Carcinogenesis 15, 1827–32, (1994)).

Aryl ether derivatives of fluorescein have not been reported as substrates for cytochrome P450 enzymes. A benzyl ether derivative of fluorescein, benzyloxyfluorescein benzyl ester, has been reported as an intermediate in the synthesis of fluorescein labeled polymers (Hargreaves and Webber, Can. J. Chem. 63, 1320–1327 (1985)), chiral pro-dyes (Tadic and Brossi, Heterocycles 31, 1975–1982, (1990)), and dye precursors (Dombrowski Jr. et al. U.S. Pat. No. 5,196,297).

easily O-dealkylated by the enzyme, and 2) a fluorescein core for ease in fluorescence detection.

The enzyme reaction and assay method which describe the invention are illustrated in Reaction Scheme 1, below. Cytochrome P450 enzymes catalyze the dealkylation of compounds of Formula I to the intermediate of Formula II. Addition of base to the assay mixture hydrolyzes the ester intermediate (if present) to fluorescein which is quantitated spectrofluorometrically.

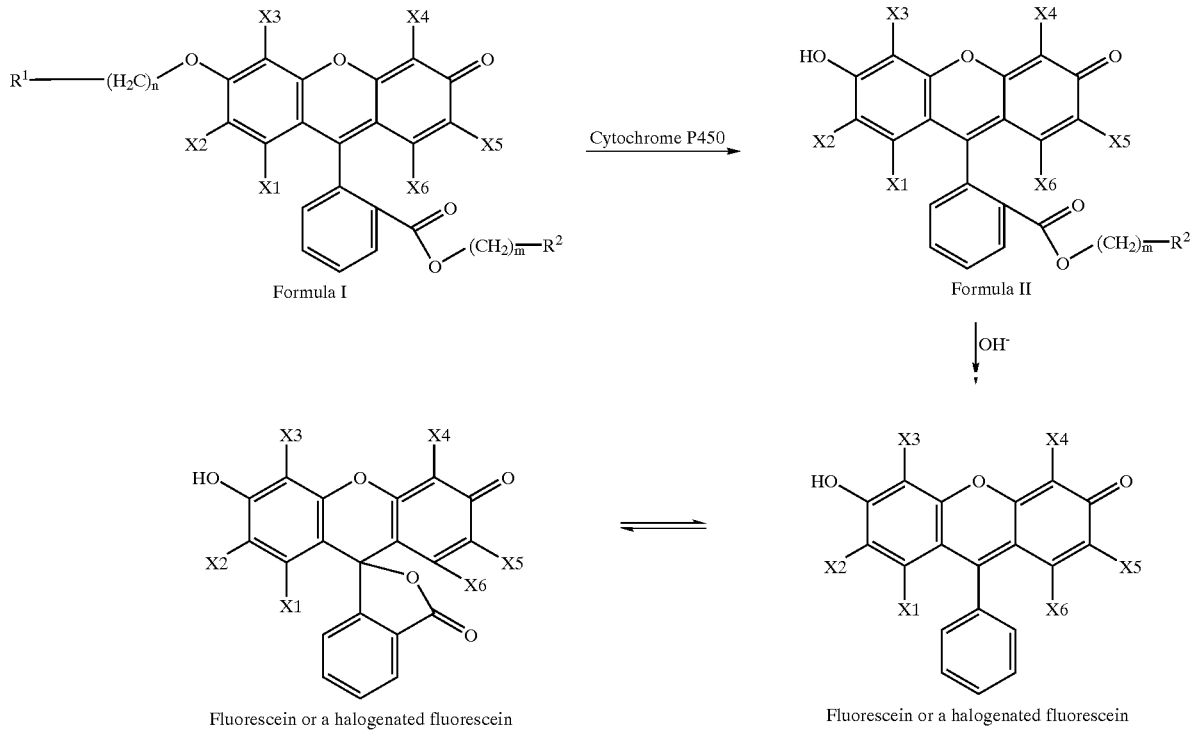

Reaction Scheme I:

SUMMARY OF THE INVENTION

The present invention relates to novel fluorescent substrates of cytochrome P450 enzymes. These substrates are useful in assessing cytochrome P450 enzyme activity and in selecting compounds which inhibit cytochrome P450 enzyme activity. Accordingly, the compounds and methods of the invention are useful for identifying potential adverse drug interactions which are mediated by inhibition of cytochrome P450 enzyme activity.

The compounds of the invention are substrates that are characterized in having properties which permit the sensitive quantitation of CYP2C8, CYP2C9, CYP2C19, and CYP3A activity using in situ fluorescence analysis. To satisfy these requirements, the compounds of the invention include: 1) An aryl ether group at position 6 of fluorescein which can be According to one aspect of the invention, compounds of Formula A are provided:

Formula A:

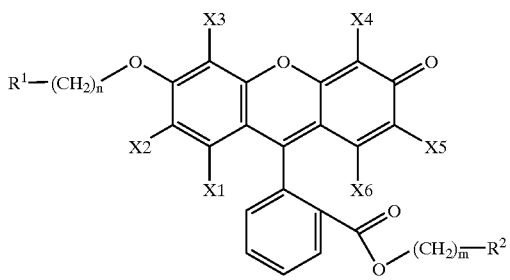

(a) wherein R1 and R2 are independently selected from the group consisting of an hydrido and an aryl, provided that R1 and R2 are not both hydrido; and wherein the aryl contains an aryl ring carbon and/or an aryl ring nitrogen and the $(CH_2)_n$ or $(CH_2)_m$ is coupled via a covalent bond to the aryl ring carbon or the aryl ring nitrogen;

(b) wherein n is 0, 1, 2, or 3;

(c) wherein X1, X2, X3, X4, X5, and X6 are independently selected from the group consisting of an hydrido, a chloro, a fluoro, a bromo, and an iodo, provided that when R1 and R2 are phenyl, and n and m are 1, at least one of X1, X2, X3, X4, X5, and X6 is not hydrido;

(d) wherein m is 0, 1, 2, or 3; and (e) wherein the compound is a cytochrome P450 substrate or a cytochrome P450 reaction product.

The above structure embraces three preferred embodiments, which are referred to herein as: (1) compounds of Formula I; (2) compounds of Formula II; and (3) compounds of Formula III. Compounds of Formula I and III are substrates for cytochrome P450 enzymes; compounds of Formula II are the products of a cytochrome P450 reaction in which a compound of Formula I is the substrate, i.e., the compounds of Formula II can be produced by the process of contacting a compound of Formula I with a cytochrome P450 under conditions whereby the cytochrome P450 enzyme catalyzes the conversion of the substrate to the reaction product.

According to certain embodiments, compounds of Formula I are provided:

Formula I:

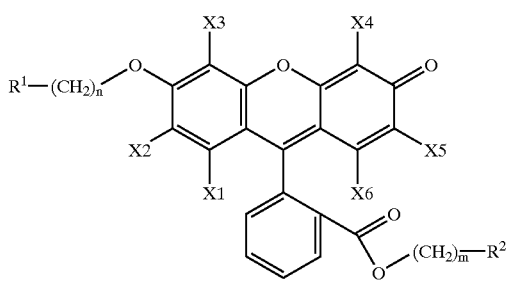

(a) wherein R1 is aryl and R2 is independently selected from the group consisting of an hydrido and an aryl, provided that R1 and R2 are not both phenyl when n and m are 1; and wherein the aryl contains an aryl ring carbon and/or an aryl ring nitrogen and the $(CH_2)_n$ or $(CH_2)_m$ is coupled via a covalent bond to the aryl ring carbon or the aryl ring nitrogen;

(b) wherein n is 0, 1, 2, or 3;

(c) wherein X1, X2, X3, X4, X5, and X6 are independently selected from the group consisting of an hydrido, a chloro, a fluoro, a bromo, and an iodo;

(d) wherein m is 0, 1, 2, or 3; and (e) wherein the compound is a cytochrome P450 substrate.

In the most preferred embodiments of the compound of Formula I, X2 and X5 are chloro and/or fluoro. In yet other embodiments, X2 and X5 may or may not be halogenated (particularly chloro and/or fluoro) and one or both of R1 and R2 are phenyl when one or both of n and m are 1. In still other preferred embodiments one or both of R1 and R2 are phenyl when one or both of n and m are 1, and the phenyl further includes (e.g., at the para position) an electron donating group, such as a halogen (especially chloro, fluoro), C (halogen)$_3$, or $NH_3^+$.

According to yet other embodiments, compounds of Formula II are provided:

A3. The compound of claim A1, having Formula II:

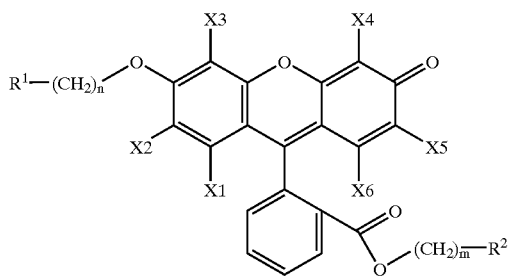

(a) wherein R1 is hydrido and R2 is an aryl; and wherein the aryl contains an aryl ring carbon and/or an aryl ring nitrogen and the $(CH_2)_m$ is coupled via a covalent bond to the aryl ring carbon or the aryl ring nitrogen;

(b) wherein n is 0;

(c) wherein X1, X2, X3, X4, X5, and X6 are independently selected from the group consisting of an hydrido, a chloro, a fluoro, a bromo, and an iodo;

(d) wherein m is 0, 1, 2, or 3; and (e) wherein the compound is a cytochrome P450 reaction product.

For the most preferred embodiments of the compound of Formula II, X2 and X5 are chloro and/or fluoro. In yet other embodiments, X2 and X5 may or may not be halogenated (particularly chloro and/or fluoro), R2 is phenyl and m is 1. In still other preferred embodiments R2 is phenyl, m is 1, and the phenyl further includes (e.g., at the para position) an electron donating group, such as a halogen (especially chloro, fluoro), C (halogen)$_3$, or $NH_3^+$.

A particularly preferred embodiment of the compound of Formula II is compound IIa:

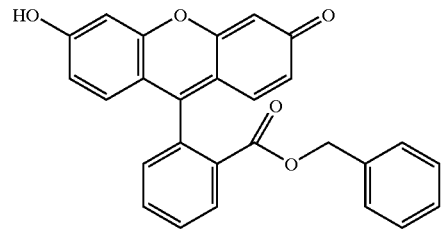

Compound IIa

According to still other embodiments, compounds of Formula III are provided:

Formula III:

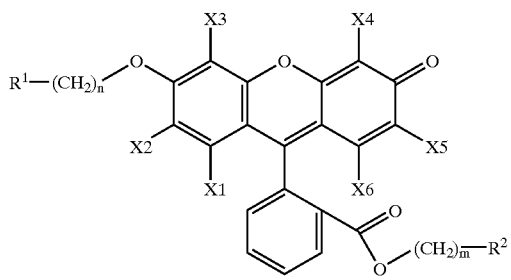

(a) wherein R1 and R2 are each phenyl; and wherein the phenyl contains an aryl ring carbon and the $(CH_2)_n$ or $(CH_2)_m$ is coupled via a covalent bond to the aryl ring carbon;

(b) wherein n is 1;
(c) wherein X1, X2, X3, X4, X5, and X6 are independently selected from the group consisting of a chloro, a fluoro, a bromo, and an iodo;
(d) wherein m is 1; and
(e) wherein the compound is a cytochrome P450 substrate.

For the most preferred embodiments of the compound of Formula III, X2 and X5 are chloro and/or fluoro. In yet other embodiments, X2 and X5 may or may not be halogenated (particularly chloro and/or fluoro). In still other preferred embodiments R2 is phenyl and the phenyl further includes (e.g., at the para position) an electron donating group, such as a halogen (especially chloro, fluoro), C (halogen)$_3$, or $NH_3^+$.

According to yet another aspect of the invention, a composition comprising a compound of Formula I, a compound of Formula II, a compound of Formula III, and/or Benzyloxyfluorescein benzyl ester ("DBF"; 97744-44-0; Benzoic acid, 2-[3-oxo-6-(phenylmethoxy)-3H-xanthen-9-yl]-benzyl ester (CA index name), Hargreaves, J. S. and S. E. Webber (1985) Can. J. Chem. 63, 1320–1327)) is provided. The compound is present in the composition at a concentration greater than at least 50% by weight. The most preferred compositions contain a concentration of the compound of Formula I, II, III, or DBF that is at least 80%, more preferably at least 90%, and most preferably at least 95% by weight. Preferably, the compositions are aqueous preparations which are free of contaminants that would interfere with a cytochrome P450 enzyme reaction. Certain embodiments of the preferred compositions are also substantially free of detectable reaction product, i.e., the compositions of the invention do not contain levels of the cytochrome P450-catalyzed reaction product. In these and other embodiments, the compositions optimally further contain a cytochrome P450, e.g., an isolated enzyme or a microsome expressing a cDNA expressed cytochrome P450.

The compositions may be contained in vials that are components of a kit for assaying cytochrome P450 enzyme activity. The vials may contain preselected amounts of the compositions to facilitate dissolution of the contents to achieve a preselected concentration of the compound for performing a cytochrome P450 enzyme assay. Accordingly, in certain embodiments of the invention, the compositions contain the appropriate buffers for performing an enzyme reaction in which the compound of Formula I, the compound of Formula III, or DBF serves as the substrate to form a fluorescent product.

According to yet another aspect of the invention, a method for assaying cytochrome P450 enzyme activity is provided. The method involves contacting a cytochrome P450 enzyme with a compound of Formula I, a compound of Formula III, or DBF under conditions whereby the cytochrome P450 enzyme catalyzes the conversion of the compound (substrate) to a cytochrome P450 reaction product. Such conditions are generally known to those of ordinary skill in the art and are illustrated in the Examples.

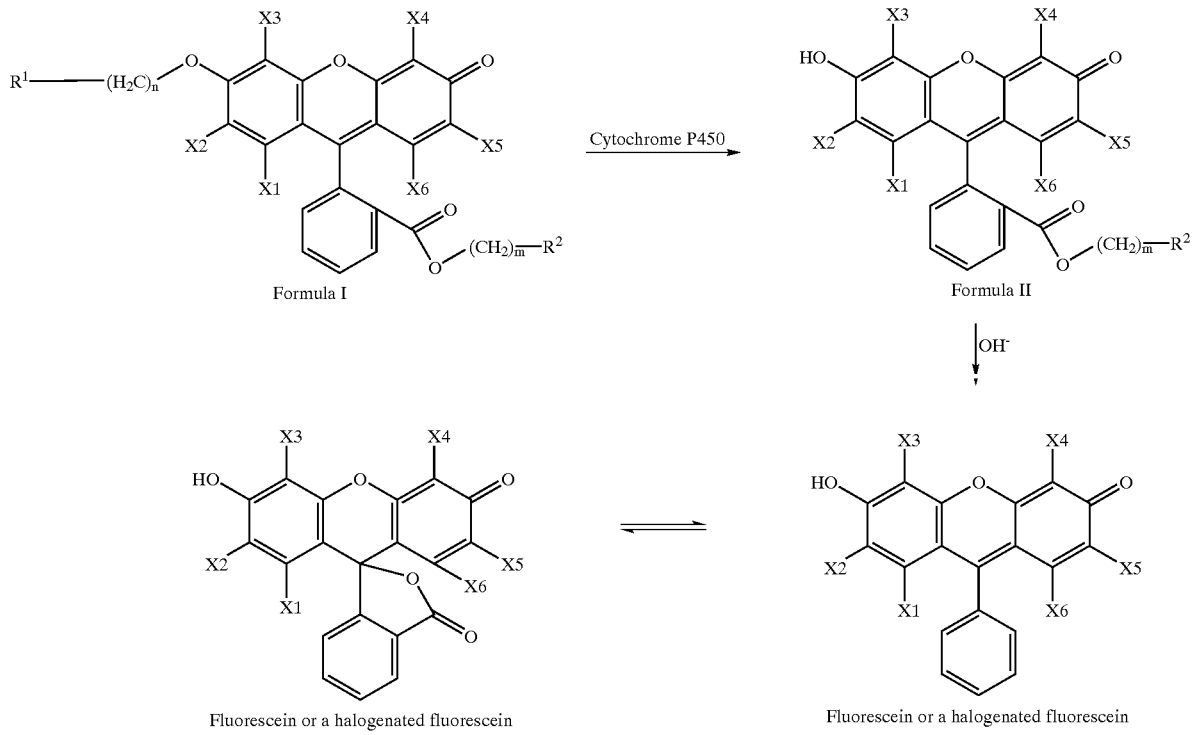

Reaction Scheme I:

Formula I

Formula II

Fluorescein or a halogenated fluorescein

Fluorescein or a halogenated fluorescein

For ease of illustration, the above reaction is shown with respect to substrates which are compounds of Formula I as defined herein. It is to be understood that the reaction also can be performed wherein the substrate is a compound of Formula III as defined herein or DBF and that these compounds optionally are halogenated as shown in their respective formulas.

The method for assaying cytochrome P450 enzyme activity is used to detect activity of a cytochrome P450 that may be contained in biological fluid sample or solid sample (e.g., a biopsy sample from liver, brain or intestine) or that may be expressed in a cell-containing or cell-free system (e.g., a microsome containing cDNA-expressed cytochrome P450). In this manner, conditions associated with deficiencies or over expression of cytochrome P450 enzyme activity can be detected.

The cytochrome P450 assay may be performed in vivo or in vitro. For example, the compounds of the invention (e.g., the compounds of Formula I, the compounds of Formula III, or DBF) can be administered to an animal model for, e.g., locating and, optionally, quantifying, cytochrome P450 enzyme activity (e.g., by observing reaction products in biological fluid or tissue samples of the animal). More preferably, the method for assaying cytochrome P450 enzyme activity is used to detect activity of a cytochrome P450 that may be contained in biological fluid sample or solid sample (e.g., a biopsy sample from liver, brain or intestine) or that may be expressed in a cell-containing or cell-free system (e.g., a microsome containing cDNA-expressed cytochrome P450). In this manner, conditions associated with deficiencies or over expression of cytochrome P450 enzyme activity can be detected. Thus, the cytochrome P450 enzyme may be contained in a sample that is a liver sample such as a crude homogenate, partially purified, or purified liver enzyme obtained from a biopsy, a cDNA-expressed cytochrome P450, in hepatocytes, or in microsomes.

According to yet another aspect of the invention, a screening method for identifying agents which inhibit cytochrome P450 enzyme activity is provided. The method involves contacting a cytochrome P450 enzyme with a compound of Formula I, a compound of Formula III , or DBF in the presence of a putative cytochrome P450 enzyme inhibitor and identifying an agent which inhibits the cytochrome P450 enzyme activity as the cytochrome P450 enzyme inhibitor. In the preferred embodiments, the screening method is a high throughput screening assay. More preferably, the screening assay is performed in a multiwell (e.g., microtiter) plate or a container for containing a relatively small volume, e.g., the compound of Formula I, Formula III, or DBF is contacted with the putative cytochrome P450 enzyme inhibitor and the cytochrome P450 enzyme in a microtiter plate well or a small vial. In certain embodiments, the compounds of Formula I, Formula III, or DBF can be provided in the microtiter plate well or small vial. For example, the compounds can be distributed into one or more vials, which are then lyophilized or otherwise dried to provide a product having an enhanced shelf life. If the product is provided for use in a kit for measuring cytochrome P450 enzyme activity, the kit can further contain instructions for redissolving the compounds of Formula I, Formula III, or DBF and, optionally, an appropriate buffer (e.g., enzyme reaction buffer) for effecting the dissolution.

According to another aspect of the invention, a method for visualizing a cytochrome P450 enzyme is provided. The method involves contacting a cytochrome P450 enzyme-containing sample with a compound of Formula I, a compound of Formula III, or DBF and subjecting the cytochrome P450 enzyme and the compound to conditions whereby the cytochrome P450 enzyme catalyzes the conversion of the compound of Formula I , the compound of Formula III, or DBF to a fluorescent product. In the preferred embodiments, the method for visualizing a cytochrome P450 enzyme is performed on a tissue section sample, i.e., the cytochrome P450 enzyme-containing sample is a tissue section such as derived from a biopsy sample.

According to still another aspect of the invention, kits for detecting and/or measuring cytochrome P450 enzyme activity are provided. The kits contain a compound of Formula I, Formula III, and/or DBF and instructions for using the kits to measure cytochrome P450 enzyme activity. The kits may further contain instructions for calculating $K_i$ and/or $IC_{50}$ for a cytochrome P450 inhibitor. The preferred compounds of Formula I and compounds of Formula III are compounds which have a high specificity of binding for the enzyme and for which the enzyme exhibits a high rate of substrate turnover. These parameters typically are reflected in the Km and Vmax values for the enzyme-catalyzed conversion of the substrate (i.e., compound of the invention) to a fluorescent product. In general, a higher relative affinity of the cytochrome P450 enzyme for a first substrate compared to a second substrate is indicated by a lower Km value for the first substrate compared to the second substrate. A higher catalytic turnover for a first substrate compared to a second substrate is indicated by a higher Vmax for the first substrate. The preferred compounds of the invention have a Km of greater than about 0.50 uM with a Vmax greater than about 0.05 $min^{-1}$. In general, the compounds of the invention have a Km from about 0.5 uM to about 5 uM and a Vmax from about 0.10 or from about 0.20 to about 50 $min^{-1}$, with a preferred range for Km being greater than about 0.50 uM and a preferred range for Vmax being from about 0.20 $min^{-1}$ to about 50 $min^{-1}$; with Vmax being more preferably from about 2.0 or from about 20.0 to about 50 $min^{-1}$.

According to yet another aspect of the invention, novel cytochrome P450 fluorescent products are provided. The novel products are compounds of Formula A wherein R1 is hydrido and n is 0 (see Formula II). In general, these novel products are produced as a reaction product of the cytochrome P450-catalyzed reaction of a substrate that is a compound of Formula I, a compound of Formula III, or DBF. In general, these compounds have structures that differ from those of the compounds of Formula I, Formula III, and DBF in having a hydroxy group at position 6 of the fluorescein.

These and other aspects of the invention as well as various advantages and utilities will be more apparent with reference to the detailed description of the preferred embodiments. All patents, patent publications and references identified in this document are incorporated in their entirety herein by reference.

BRIEF DESCRIPTION OF THE DRAWINGS

The drawings are illustrative only and are not required for enablement of the claimed invention.

DETAILED DESCRIPTION OF THE INVENTION

I. Definitions

Figure 1:
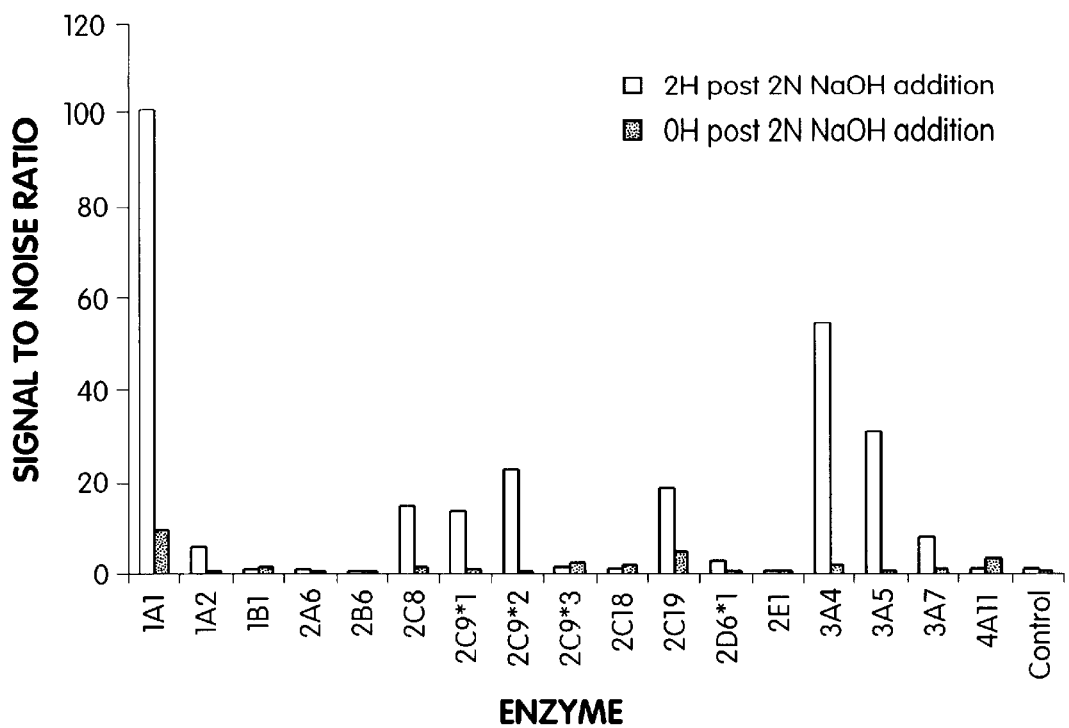
FIG. 1 shows selectivity for Compound 1a dealkylation by a panel of Human P450 enzymes and Effect of Delay in Read Time following addition of 2N Stop Solution on Signal to Noise Ratio.

Throughout this document cytochrome P450 is used in reference to the enzyme which catalyzes the conversion of a compound of the invention to a fluorescent product. It is to be understood that any member of the cytochrome P450 family can be used in any of the enzyme reactions discussed herein and that CYP2C8, CYP2C9, CYP2C19, and CYP3A4 represent a particularly preferred embodiment of the invention.

Molecular terms, when used in this application, have their common meaning unless otherwise specified. The term hydrido denotes a single hydrogen atom.

Aryl groups can contain from 0–4 hetero atoms selected from oxygen, nitrogen and sulfur in a single or fused carbocyclic or heterocyclic ring system, having from 5–15 ring members. One or more hydrogen atoms may also be replaced by a substituent group selected from an acyl, an amino, a carboalkoxy, a carboxy, a carboxyamido, a cyano, a halo, a hydroxy, a nitro, a thio, an alkyl, an aryl, a cycloalkyl, an alkoxy, an aryloxy, a sulfoxy, and a guanido group. When the aryl group is coupled to a linker such as $(CH_2)_n$ or $(CH_2)_m$, a carbon or a nitrogen of the aryl ring is covalently coupled to the linker.

A preferred class of aryl groups are unsubstituted phenyl groups and phenyl groups in which one or more hydrogen have been replaced with an alkyl, alkoxy, aryloxy, or halo group. Exemplary aryl groups include phenyl, phenyl naphthyl, biphenyl, terphenyl, pyridinyl, and various other phenyl derivatives.

II. Description

The invention provides compounds of Formula A and methods for manufacturing and/or using the compounds of Formula I, II, III, and DBF for assaying the activity of cytochromes P450. The compounds are particularly useful for measuring the potential inhibition of cytochromes P450, preferably in a high throughput screening assay. For example, the invention provides a method for assaying cytochromes P450 which involves contacting a cytochrome P450 enzyme with a compound of Formula I, a compound of Formula III, or DBF under the conditions in which the cytochrome P450 enzyme interacts with the compound and catalyzes dealkylation at the 6 position of the compound to form a 6-hydroxy-fluorescein ester product. Such conditions are known to those skilled in the art (see also, e.g., the Examples for conditions). This method can be performed using in vivo or in vitro sources of cytochrome P450 enzyme. In a further aspect, the invention provides a method for assessing the potential cytochrome P450 inhibition of a test chemical, preferably in a high throughput screening assay.

The structures of the compounds of the invention, particularly the structures of Formula A, Formula I, Formula II, and Formula III, are provided in the Summary and in the Claims.

GENERAL SYNTHETIC PROCEDURES

For ease of illustration, the reaction illustrated below are shown with respect to substrates which are compounds of Formula I. It is to be understood that the reaction also can be performed wherein the substrate is a compound of Formula III or DBF and that these compounds optionally are halogenated as shown in their respective formulas.

General Procedure 1

Compounds of Formula I and Formula III are synthesized based on the method of Hargreaves and Webber (Can. J. Chem. 63, 1320–1327 (1985)). The commercially available reagent, fluorescein (compound 1), is converted to a compound of Formula I or a compound of Formula III by treatment with compound 2 and reagent A in an appropriate solvent such as tetrahydrofuran, acetone, dimethyl sulfoxide, acetonitrile, or dimethylformamide at temperatures ranging from 0° C. to 100° C.

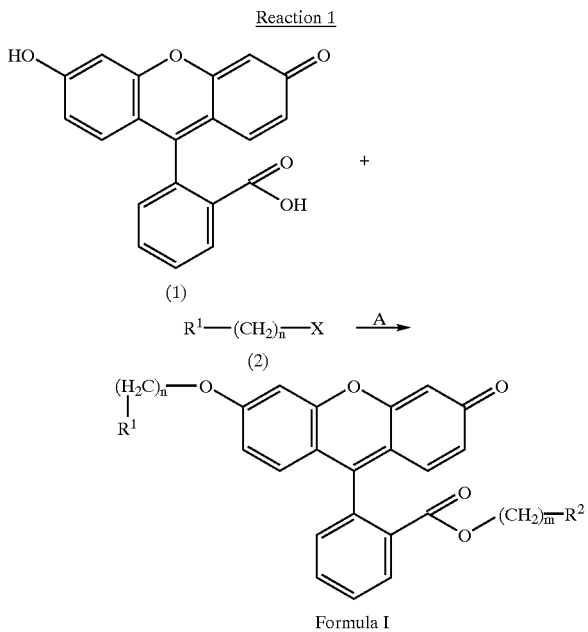

Reaction 1 wherein R1, R2, n, and m are defined as above; wherein A is a base such as potassium carbonate or lithium hydroxide; and X is a leaving group such as bromide, chloride, iodide, or tosylate.

General Procedure 2

A compound of Formula I, is converted to another compound of Formula I by treatment with reagent B in an appropriate organic solvent such as tetrahydrofuran, acetone, dimethylsulfoxide, acetonitrile, or dimethylformamide mixed with water at temperatures ranging from 0° C. to 100° C. A preferred compound for performing this reaction is benzyloxyfluorescein benzyl ester (compound IIa, also referred to herein as "DBF") to yield a preferred compound of Formula I, Compound Ib (MBF).

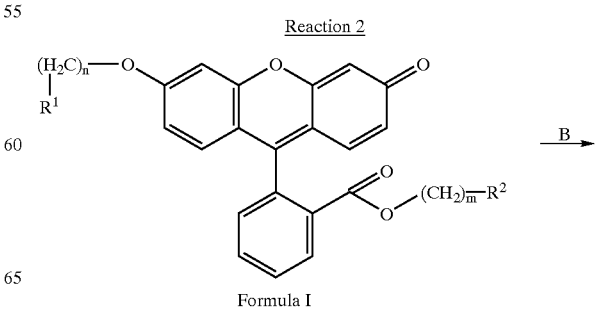

Reaction 2

-continued

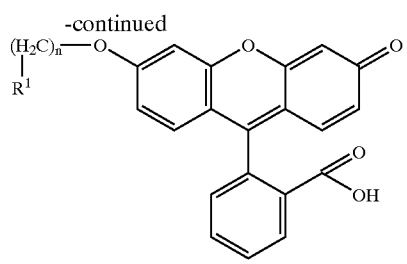

wherein R1 is defined as above; wherein B is a base such as sodium hydroxide or lithium hydroxide.

EXAMPLES

The following examples are detailed descriptions of the methods of making and using the compounds of Formula A. These detailed preparations fall within the scope of, and serve to exemplify, the above described General Procedures which form part of the invention. These Examples are presented for illustrative purposes only and are not intended to limit the scope of the invention.

Example 1
Preparation of O-Benzylfluorescein Benzyl Ester (DBF). (Compound Ia)

Fluorescein (40 g, 120.5 mmol) was dissolved in dimethylformamide (DMF, 500 mL) in a 2 L flask fitted with a mechanical stirrer then potassium carbonate (72 g, 521.7 mmol) was added in as a single portion. The reaction was heated to 80° C. then benzyl chloride (42 mL, 363.5 mmol) was added dropwise. After 24 h at 80° C. the reaction was cooled down to room temperature. Acetone (400 mL) was added and the product was allowed to precipitate overnight. The solid orange product was filtered, washed with acetone and dried in a vacuum oven at 50° C. The O-benzylfluorescein benzyl ester was obtained as an orange solid (36.4 g, 59%): mp 192–193° C. (Lit. 193–194° C.); $^1$H NMR (DMSO-$d_6$): 4.97 (dd, 2H, J=12.2 Hz, J=15.3 Hz), 5.28 (s, 2H), 6.13 (d, 1H, J=1.9 Hz), 6.36 (dd, 1H, J=9.9 Hz), 6.77 (d, 1H, J=9.9 Hz), 6.82 6.77 (d, 1H, J=9.0 Hz), 6.90–6.98 (m, 3H), 7.14–7.27 (m, 4H), 7.33–7.52 (m, 6H), 7.78 (dt, 1H, J=1.65 Hz, J=7.4 Hz), 8.23 (dd, 1H, J=1.35 Hz, J=7.7 Hz); $^{13}$C NMR (DMSO-$d_6$): 67.4, 70.7, 101.9, 105.2, 114.7, 115.0, 117.3, 128.3, 128.5, 128.7, 128.8, 128.9, 129.4, 130.0, 130.2, 130.6, 130.8, 131.2, 131.4, 133.8, 134.1, 135.3, 136.6, 150.1, 153.9, 158.7, 163.3, 165.5, 184.4; IR (nujol) cm–1 1728, 1643, 1595, 1517, 1462, 1377, 1261, 1211, 1081, 855. $C_{34}H_{24}O_5$: Calc.(C, 79.67; H, 4.72) Found (C, 79.74; H, 4.79).

EXAMPLE 2
Preparation of Monobenzyl Fluorescein (MBF) Compound Ib

O-Benzylfluorescein benzyl ester, compound Ia (20.0 g, 39 mmol), was dissolved in THF/$H_2O$ 10/1 (400 mL) and lithium hydroxide monohydrate (6.0 g, 158 mmol) was added. The reaction was refluxed for two hours then cooled down to room temperature. The lithium salt was removed by filtration, and the filtrate was diluted in water and extracted with methylene chloride. The organic phase was dried over magnesium sulfate and evaporated under reduced pressure followed by drying in a vacuum oven at 60° C. The monobenzyl fluorescein was obtained as a yellow solid (11.9 g, 70%): mp 113–115° C.; $^1$H NMR (DMSO-$d_6$): 5.17 (s, 2H), 6.58 (s, 2H), 6.64–6.71 (m, 2H), 6.68 (dd, 1H, J=2.2 Hz, J=8.8 Hz), 7.02 (d, 1H, J=2.2 Hz), 7.26–7.47 (m, 6H), 7.72 (t, 1H, J=7.2 Hz), 7.79 (t, 1H, J=7.4 Hz), 8.01 (d, 1H, J=7.7 Hz), 10.18 (s, 1H); $^{13}$C NMR (DMSO-$d_6$): 70.2, 83.2, 102.2, 102.8, 110.0, 111.8, 113.1, 113.4, 124.6, 125.2, 126.6, 128.3, 128.6, 129.0, 129.6, 129.7, 130.7, 136.2, 137.1, 152.3, 153.0, 160.1, 160.6, 169.2; IR (nujol) cm-1 1727, 1609, 1501, 1462, 1378, 1286, 1249, 1172, 1108. $C_{27}H_{18}O_5$: Calc.(C, 76.28; H, 4.34) Found (C, 76.22; H, 4.32).

TABLE I

| # | Structure | General Procedure |
|---|-----------|-------------------|
| Ia | [structure of Ph-O-xanthene-benzoate-O-CH2-Ph] | 1 |
| Ib | [structure of Ph-O-xanthene-benzoic acid] | 2 |

B. Biological Evaluation of Compound I

The evaluation of compounds of Formula I for usefulness as cytochrome P450 substrates includes: (1) The specificity of the compounds of Formula I as substrates for individual cytochromes P450 was examined using cDNA-expressed cytochromes P450; (2) Enzyme kinetics for the compounds of Formula I were performed using cDNA-expressed cytochromes P450; and (3) The $IC_{50}$ values for known inhibitors of cytochromes P450, measured in a high throughput screening assay, of compounds of Formula I, were correlated with those values from known substrates useful for this application.

(1) Substrate Specificity

Figure 2:
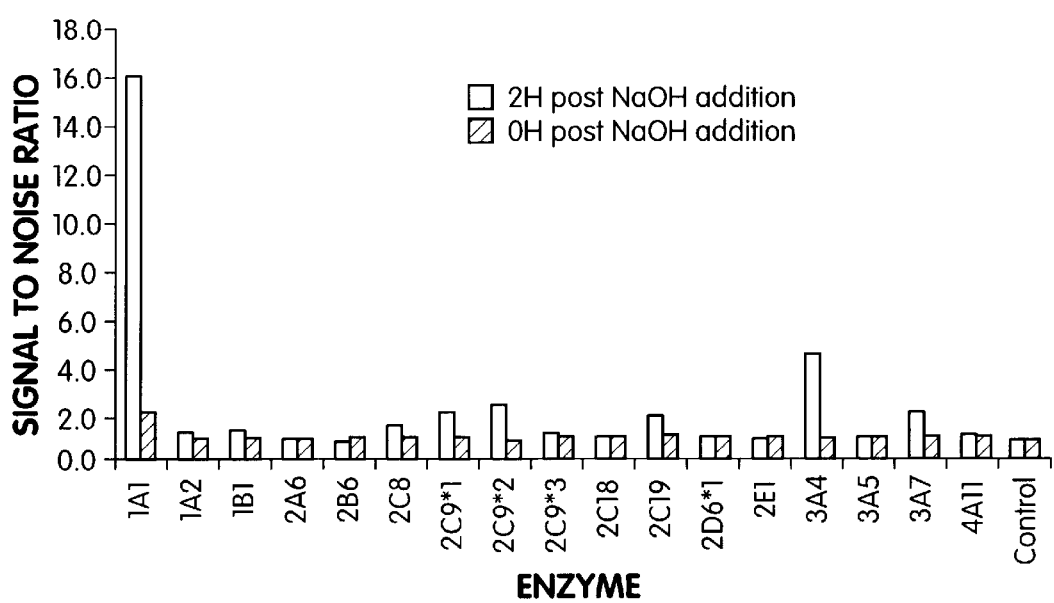
FIG. 2 shows selectivity for Compound 1b dealkylation by a panel of Human P450 enzymes and Effect of Delay in Read Time following addition of 2N Stop Solution on Signal to Noise Ratio.
Figure 3A:
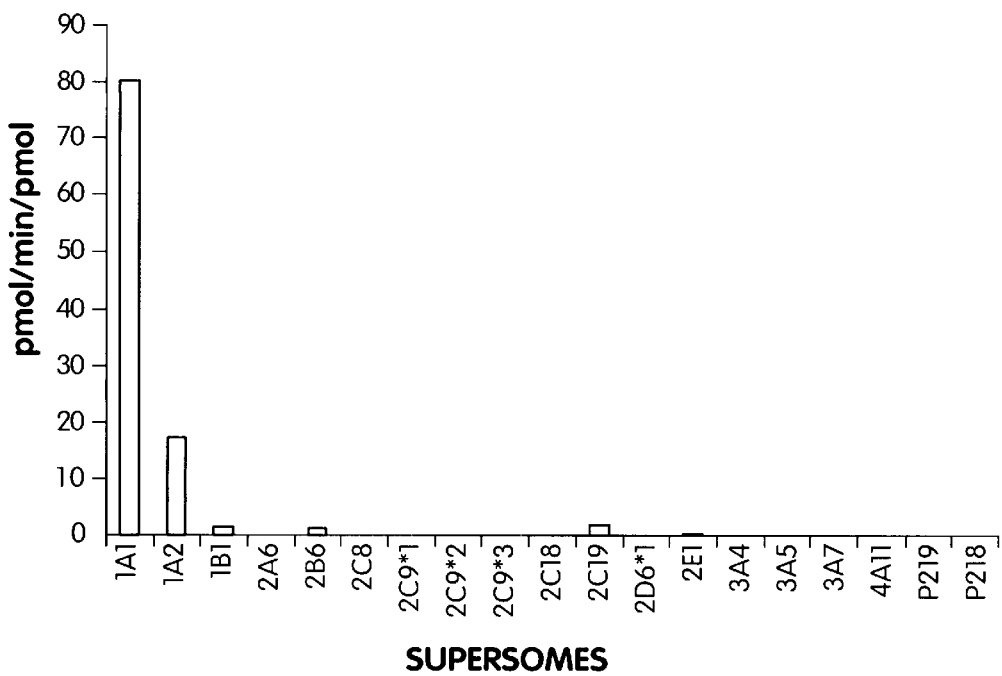
FIG. 3A shows selectivity for CEC* dealkylation in a panel of human P450 enzymes.
Figure 3B:
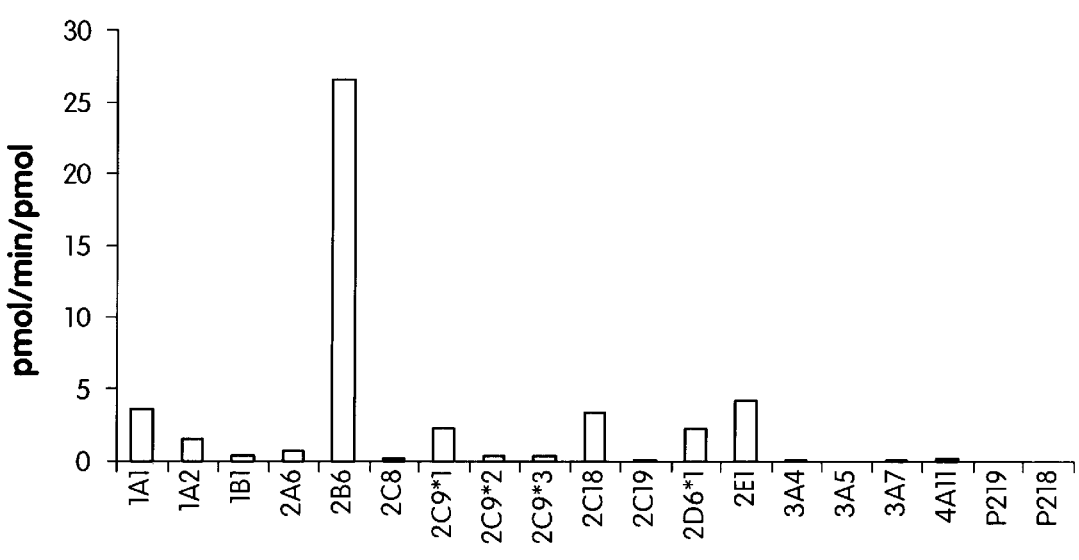
FIG. 3B shows selectivity for MFC* dealkylation in a panel of human P450 enzymes.
Figure 3C:
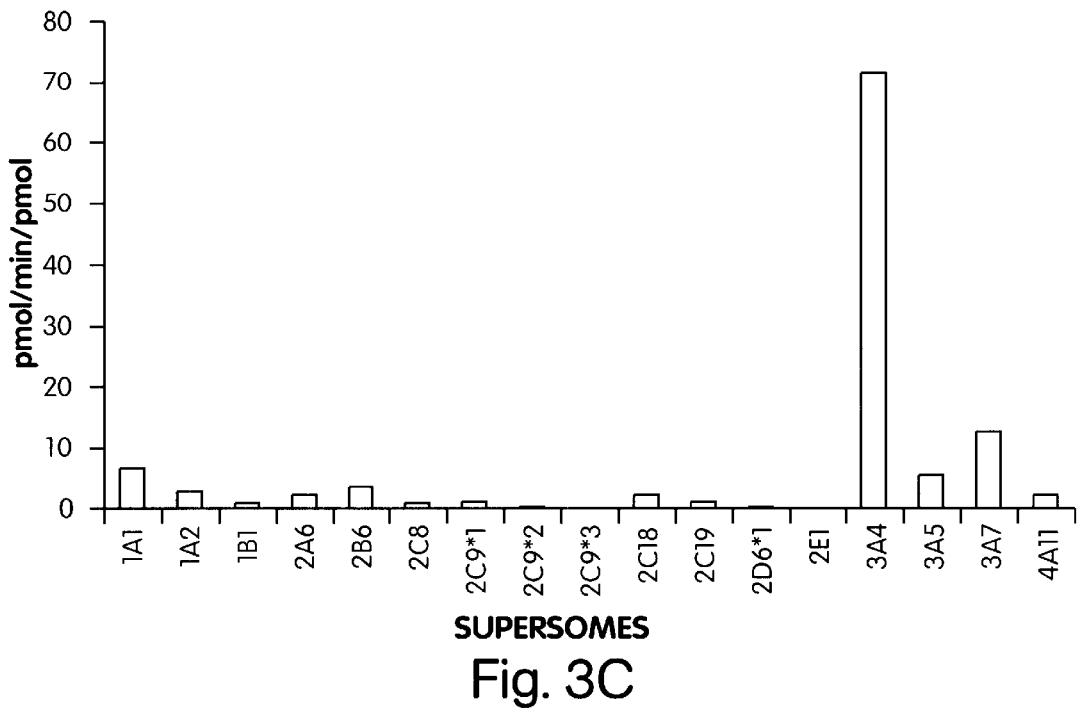
FIG. 3C shows selectivity of 7-BQ* dealkylation in a panel of human P450 enzymes.
Figure 3D:
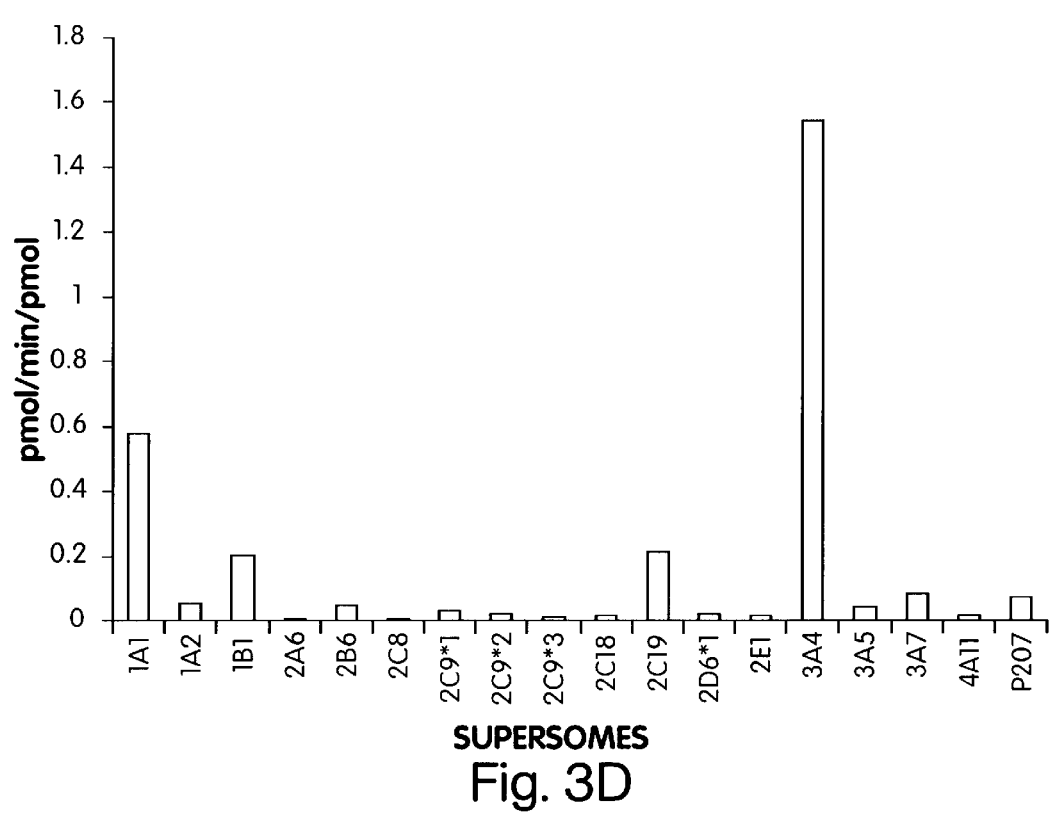
FIG. 3D shows selectivity for BFC* dealkylation in a panel of human P450 enzymes.
Figure 3E:
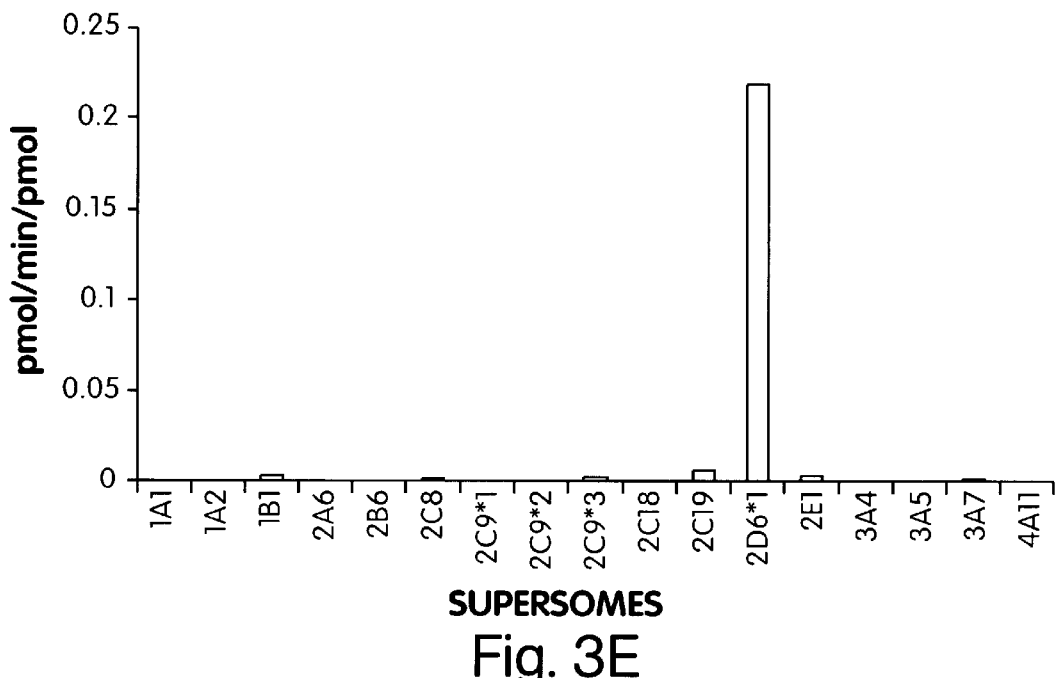
FIG. 3E shows selectivity for AMMC* dealkylation in a panel of human P450 enzymes.
Figure 3F:
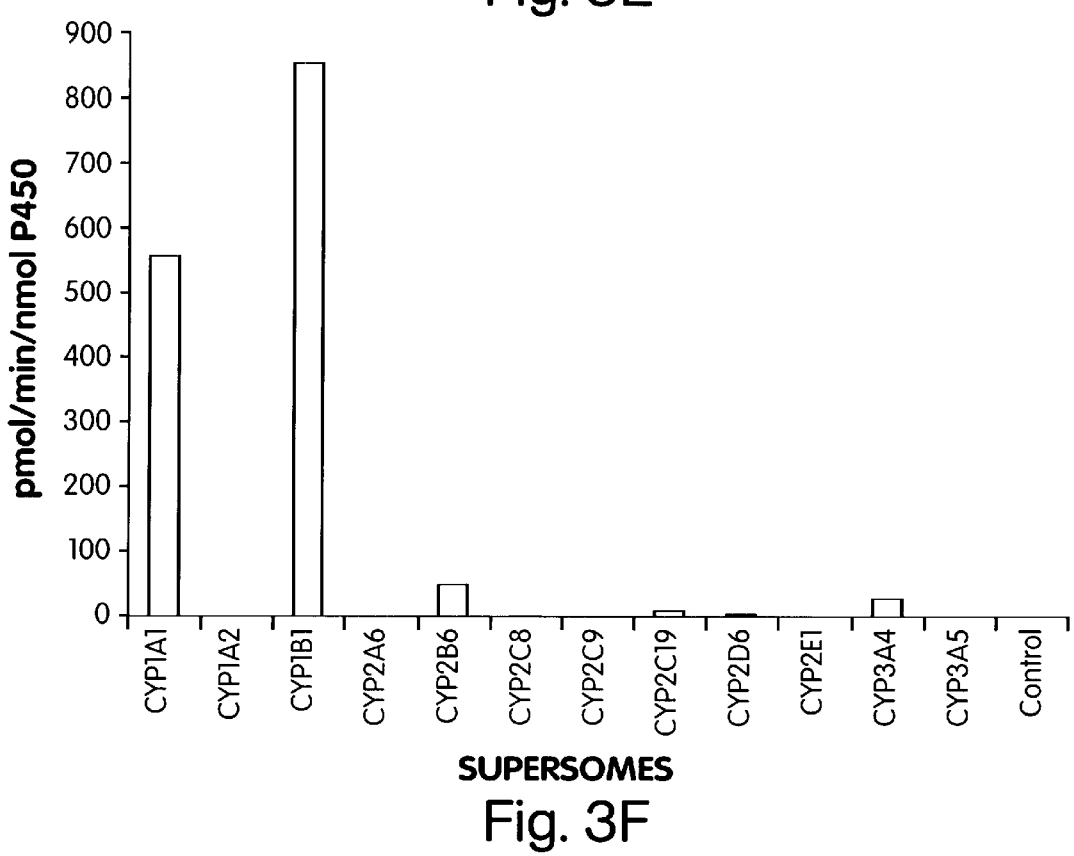
FIG. 3F shows selectivity for dealkylation of Benzyloxyresorufin in a panel of human P450 enzymes.

The specificity of several cytochrome P450 enzymes for the dealkylation of Compound Ia (FIG. 1) and Compound Ib (FIG. 2) was examined. Compounds of Formula I are substrates for multiple isoforms within the three major families of drug metabolizing P450 enzymes (as demonstrated by a high signal to noise ratio). While it is well known that fluorescein fluorescence is best detected at high pH (>9), a novel aspect of this assay, which contrasts with previously described fluorescence-based assays, is that the signal to noise ratio was dramatically increased when the microtiter plate readings were taken 2 hours after the reaction was stopped by the addition of 2N sodium hydroxide solution (2N NaOH).

CYP1A1 has the highest activity with compound Ia. CYP2C8 also exhibits substantial enzyme activity for Compound Ia. This is the first fluorescent substrate ever reported for CYP2C8. CYP2C9* 1, CYP2C19, and members of the CYP3A family also catalyzed the dealkylation of compound Ia. Compound Ia is a more sensitive substrate (higher signal to noise ratio) for CYP2C9 and CYP2C19 compared to the previously described alkylcoumarin fluorescent substrates. Compound Ib as a substrate for the various P450s gave substantially less signal versus Compound Ia and exhibited roughly a similar enzyme specificity profile. For the fluorometric assay of cytochromes P450 CYP1A1, CYP2C8, CYP2C9, CYP2C19, and CYP3A, compound Ia is clearly superior to compound Ib.

Example Compounds Ia and Ib. Assays were conducted in 96 well microtiter plates (Corning COSTAR, cat. no. 3915). The substrate, compound Ia, was prepared in acetonitrile. After cofactors addition, the plates were prewarmed to 37° C. Incubations were initiated by the addition of prewarmed enzyme and substrate. The enzymes were commercially available, baculovirus/insect cell expressed human P450s (SUPERSOMES®, GENTEST Corporation). The amount of enzyme added per well was 2 pmole. The final cofactor concentrations were 1.3 mM NADP, 3.3 mM glucose-6-phosphate and 0.4 U/mL glucose-6-phosphate dehydrogenase. Final incubation volume was 0.2 ml. Incubations were carried out for 30 minutes and stopped by the addition of 0.075 mL of 2 N sodium hydroxide solution. Fluorescence per well was measured using a BMG FLUOstar fluorescence plate scanner equipped with an IBM-compatible computer. The metabolite was measured using an excitation wavelength of 485 nm and emission wavelength of 530 nm. Data was exported and analyzed using an Excel spreadsheet.

(2) Enzyme Kinetics

The evaluation of compounds of Formula I were performed by measuring the kinetics of turnover using cDNA-expressed cytochromes P450 CYP3A4 and CYP2C8. Vmax and Km values are important for the optimization of the assay conditions and for setting the parameters for inhibition experiments. Fluorometric assays for the turnover of compounds of Formula I by cytochromes P450 were performed based on a modification of the method by Crespi et al. *Anal Biochem.* 248, 188–190, (1997).

Comparisons of the CYP3A4 enzyme kinetics for compound Ia and the fluorescent substrate, 7-benzyloxyresorufin (BzRes), show that CYP3A4 has a higher affinity for compound Ia (lower Km) and a higher catalytic turnover for compound Ia (higher Vmax) (See Table II). Additionally, compound Ia is a more robust substrate in terms of solubility and product detection properties. Based on these results, compound Ia is a better fluorescent substrate for CYP3A4 than the previously described BzRes.

TABLE II

| Substrate | Enzymes | Km (uM) | Vmax |
|---|---|---|---|
| Ia | CYP3A4 | 0.87 ± 0.12 | 22 ± 0.98 |
| BzRes | CYP3A4 | 30 ± 7 | 2.3 ± 0.2 |

For CYP2C8, the Km was found to be 1.4 uM and the Vmax was determined to be 0.22 min$^{-1}$. These parameters are reasonable allowing this assay to be utilized for high throughput fluorescent assays using microtiter plates. As stated earlier, this is the first fluorescent substrate reported for this important human cytochrome P450 enzyme.

CYP2C8 is the human cytochrome P450 primarily responsible for the metabolism of the anti-cancer drug paclitaxel (TAXOL™, Rahman, et al., 1994. *Cancer Research.* 54, 5543–5546). The structure of paclitaxel and the site of hydroxylation by CYP2C8 is shown in the figure below. Notice that this large complicated molecule does not resemble any of the fluorescent substrates described herein, including DBF.

Structure of Paclitaxel and Position of Hydroxylation

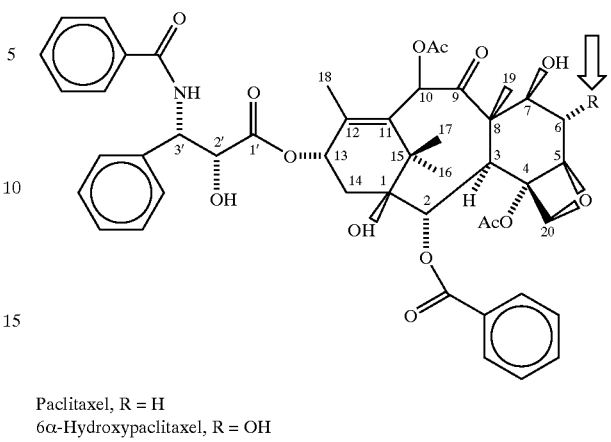

Paclitaxel, R = H
6α-Hydroxypaclitaxel, R = OH

In addition, the following fluorescent molecules have been tested as a substrate probe for CYP2C8 and the assay results obtained for these substrates (FIG. 3) further illustrate the unexpected and surprising specificity of cytochrome P450 CYP2C8 for DBF:

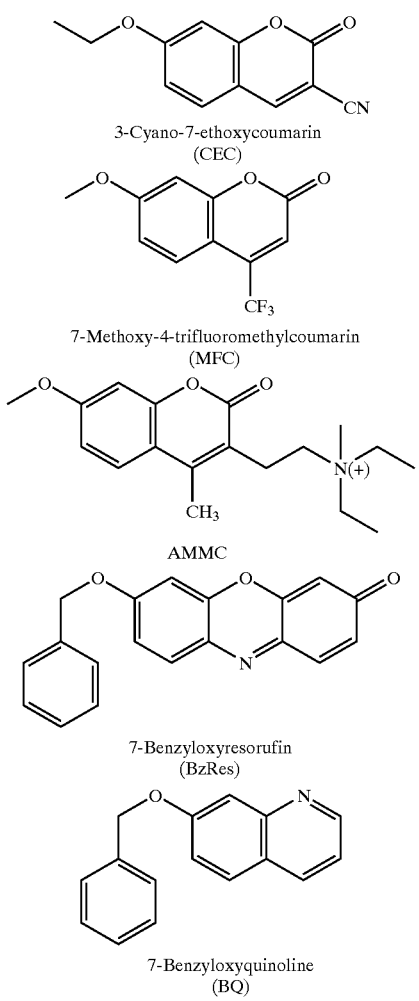

3-Cyano-7-ethoxycoumarin
(CEC)

7-Methoxy-4-trifluoromethylcoumarin
(MFC)

AMMC

7-Benzyloxyresorufin
(BzRes)

7-Benzyloxyquinoline
(BQ)

-continued

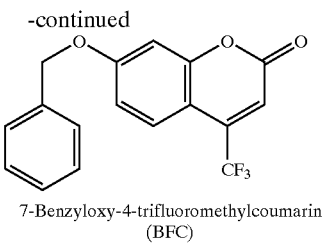

7-Benzyloxy-4-trifluoromethylcoumarin
(BFC)

Data for these specificity experiments is shown in FIG. 3 (panels 3A, 3B, 3C, 3D, 3E, and 3F. Assays were conducted in 96-well microtiter plates. Microsomes were obtained from GENTEST Corp from metabolically competent human B-lymphoblastoid cell lines that stably express rat CYP2E1 or rat CYP2A1 or from baculovirus-infected insect cells (SUPERSOMES®, all other enzymes). Substrates and metabolites were obtained from GENTEST Corporation except fluorescein which was obtained from Sigma-Aldrich. All other chemicals (reagent grade) were obtained from Sigma-Aldrich. The substrates and metabolites examined and the wavelength used for analysis are shown in Table III. Potassium phosphate buffer (0.1 mL) containing an NADPH-regenerating system was added to each well. The plate was then warmed to 37 ° C. and the reaction initiated by the addition of pre-warmed enzyme/substrate (E/S) mix. The E/S mix contained buffer, cDNA-expressed P450 (2.5–87 pmo/mL final), control protein from mock-transfected insect cells (in order to standardize protein to approximately 0.25 mg/mL final) and substrate (1.0 μM–50 μM final). Reactions were terminated after 20–45 min by addition of 75 μl 80:20 acetonitrile:0.5 M Tris base or for Compound Ia only, 2 N NaOH. The final concentration for all enzymes was 50 nM except for CYP2A1 (20 nM) and for CYP2E1 (87 nM). Fluorescence signal was measured using a FLUOstar model 403 fluorescence plate reader (BMG LabTechnologies, Inc., Durham, N.C.).

TABLE III

Fluorometric substrates and their metabolite excitation and emission wavelengths

| Substrate | Substrate Abbreviation | Metabolite | Ex (nm) | Em (nm) |
|---|---|---|---|---|
| 3-[2-(N,N-Diethyl-N-methylamino) ethyl]-7-methoxy-4-methylcoumarin | AMMC | 3-[2-(N,N-Diethyl-N-methylamino) ethyl]-7-hydroxy-4-methylcoumarin | 390 | 460 |
| 3-[2-(N,N-Diethyl-N-methylamino) ethyl]-7-methoxy-4-trifluoromethylcoumarin | MeAMFC | 3-[2-(N,N-Diethyl-N-methylamino) ethyl]-7-hydroxy-4-trifluoromethylcoumarin | 410 | 538 |
| 7-Methoxy-3-cyano-coumarin | CMC | 7-hydroxy-3-cyano-coumarin | 410 | 460 |
| 7-Ethoxy-3-cyano-coumarin | CEC | 7-hydroxy-3-cyano-coumarin | 410 | 460 |
| 7-Methoxy-4-trifluoromethylcoumarin | MFC | 7-hydroxy-4-trifluoromethylcoumarin | 410 | 538 |
| 7-Benzyloxy-4-trifluoromethylcoumarin | BFC | 7-hydroxy-4-trifluoromethylcoumarin | 410 | 538 |
| Compound Ia | 1a | Fluorescein | 485 | 538 |
| 7-Benzyloxyquinoline | BQ | 7-hydroxyquinoline | 410 | 538 |
| Resorufin benzyl ether | BzRes | Resorufin | 530 | 590 |

Example Compound Ia. Assays were conducted in 96 well microtiter plates (Corning COSTAR, cat. no. 3915). The substrate, compound Ia, was prepared in acetonitrile. After cofactors addition, the plates were prewarmed to 37° C. Incubations were initiated by the addition of prewarmed enzyme and substrate. The enzymes were commercially available, baculovirus/insect cell expressed human CYP3A4 or CYP2C8 (SUPERSOMES®, GENTEST Corporation). The amount of enzyme added per well was 0.2 pmoles (CYP3A4) or 2 pmole (CYP2C8). The final cofactor concentrations were 1.3 mM NADP, 3.3 mM glucose-6-phosphate and 0.4 U/mL glucose-6-phosphate dehydrogenase. Final incubation volume was 0.2 ml. Incubations were carried out for 10 minutes (CYP3A4) or 30 min (CYP2C8) and stopped by the addition of 0.075 mL of 2 N sodium hydroxide solution. Fluorescence per well was measured using a BMG FLUOstar fluorescence plate scanner equipped with an IBM-compatible computer. The metabolite was measured using an excitation wavelength of 485 nm and emission wavelength of 530 nm. Data was exported and analyzed using an Excel spreadsheet. The activity was quantitated by comparing to a standard curve of fluorescein. Apparent Km and Vmax values were calculated by non-linear regression using SigmaPlot software.

(3) Example I. High Throughput Cytochrome P450 Inhibition Screen—CYP3A4

Measuring the cytochrome P450 inhibition potential of compounds of Formula I was based on a modification of the published method by Crespi et al. Anal Biochem. 248, 188–190, (1997). With CYP3A4, a series of test compounds was examined in the modified system, using BzRes, 7-benzyloxy quinoline (BQ), benzyloxy trifluoromethyl coumarin (BFC) or compound Ia as a substrate (Table IV). In general, inhibitors of P450 enzymes exhibit similar $IC_{50}$ values independent of substrate. However, this in not the case with CYP3A4. A several fold range in $IC_{50}$ values was found and these results are consistent with the unusual kinetics associated with this enzyme (K E Thummel and G R Wilkinson, Ann. Rev. Pharmacol. Toxicol.38:389–430 (1998)). One explanation is that the CYP3A4 enzyme is capable of accommodating 2 or more compounds simultaneously, one of which may activate, or inhibit metabolism of the other. The use of multiple substrates (with diverse chemical properties, i.e. size, shape, etc.) to test for inhibition of CYP3A4 has been recommended. Thus, compound Ia, represents a valuable tool for exploring the potential for a drug to interact with other, co-administered drugs and CYP3A4. Moreover, the utility of Compound Ia as a CYP3A4 substrate that utilizes only small amounts of enzyme to perform the assay was also demonstrated.

The utility of compound Ia for measuring the inhibition of CYP2C8 is demonstrated in Table V. A series of 8 test compounds was examined. Values obtained are consistent with those expected. For example, sulfaphenazole exhibited an elevated IC50, compared to the $IC_{50}$ obtained with CYP2C9 (~0.22 uM), another member of the CYP2C family. Additionally, the prototypical substrate for the enzyme, paclitaxel, inhibited the turnover of compound Ia which is consistent with the conclusion that these two molecules are competing substrates for CYP2C8.

TABLE IV

Absolute and relative Mean IC50 Values for CYP3A4 with Compound Ia substrate (uM)

| Test Compound | Absolute Mean IC50 Values | | | | | | Relative Mean Values | | | |
|---|---|---|---|---|---|---|---|---|---|---|
| | BzRes | BQ | BFC | Ia | Overall | Range | BzRes | BQ | BFC | Ia |
| Itraconazole | 0.176 | 0.350 | 0.034 | 0.038 | 0.176 | 10 | 1.000 | 1.987 | 0.195 | 0.216 |
| Ketoconazole | 0.034 | 0.072 | 0.005 | 0.002 | 0.028 | 46 | 1.198 | 2.563 | 0.183 | 0.056 |
| Miconazole | 0.175 | 0.613 | 0.057 | 0.058 | 0.226 | 11 | 0.775 | 2.718 | 0.252 | 0.256 |
| Erythromycin | 1.797 | 54.443 | 4.496 | 25.344 | 21.520 | 30 | 0.084 | 2.530 | 0.209 | 1.178 |
| Cisapride | 0.107 | 0.022 | 0.022 | 0.922 | 0.268 | 41 | 0.398 | 0.083 | 0.083 | 3.436 |
| Mibefradil | 0.021 | 0.066 | 0.005 | 0.054 | 0.037 | 12 | 0.561 | 1.807 | 0.146 | 1.486 |
| Midazolam | 59.930 | 3.560 | 1.250 | 1.687 | 16.607 | 48 | 3.609 | 0.214 | 0.075 | 0.102 |
| Clotrimazole | 0.019 | 0.013 | 0.002 | 0.005 | 0.010 | 7.9 | 1.943 | 1.285 | 0.247 | 0.525 |
| Nifedipine | 68.494 | 16.782 | 8.383 | 4.132 | 24.448 | 17 | 2.802 | 0.686 | 0.343 | 0.169 |
| Cyclosporin | 1.200 | 146.885 | 3.122 | 3.307 | 38.629 | 122 | 0.031 | 3.803 | 0.081 | 0.086 |
| Verapamil | 0.398 | 8.401 | 0.357 | 4.190 | 3.336 | 21 | 0.119 | 2.518 | 0.107 | 1.256 |
| Terfenadine | Activation | 6.307 | 1.001 | 2.149 | 3.152 | 6.3 | — | 2.001 | 0.318 | 0.682 |
| a-Naphthoflavone | Activation | Activation | Activation | 146.148 | — | | — | — | — | — |
| Tamoxifen | Activation | >1000 | >1000 | >1000 | — | | — | — | — | — |
| Carbamazepine | Activation | 478.634 | 174.969 | 89.943 | 247.849 | 5.3 | | 1.931 | 0.706 | 0.363 |
| Ethynylestradiol | 6.401 | 3.752 | 1.425 | 3.319 | 3.724 | 4.5 | 1.719 | 1.008 | 0.383 | 0.891 |
| Testosterone | Activation | >1000 | Activation | 32.108 | — | | — | — | — | — |
| TAO | 0.292 | 6.105 | 0.412 | 1.925 | 2.184 | 21 | 0.134 | 2.796 | 0.189 | 0.882 |
| Progesterone | Activation | >200 | Activation | 11.501 | — | | — | — | — | — |
| Quercetin | >50 | >50 | >50 | >50 | — | | — | — | — | — |
| | | | | | Mean | 27 | 1.105 | 1.862 | 0.234 | 0.772 |

TABLE V

IC$_{50}$ Values with Compound Ia as a CYP2C8 Substrate (uM)

| Test Compound | IC$_{50}$ |
|---|---|
| Quercetin | 2.35 |
| Paclitaxel | 13.5 |
| Sulfaphenazole | 182 |
| Carbamazepine | >50 |
| Phenytoin | >50 |
| Ketoconazole | 6.65 |
| Cyclosporin | >200 |
| Diclofenac | >50 |

Example Compound Ia. Assays were conducted in 96 well microtiter plates. The substrates, compounds of Formula I, were prepared in acetonitrile. The substrate stock concentrations were twice the final concentration (final concentration chosen to be approximately the apparent $K_m$, for example 1–2 uM for compound I). The 12 wells in a row were used for one test. Wells 1 to 8 contained serial 1:3 dilutions of the inhibitors. Wells 9 and 10 contained no inhibitor and rows 11 and 12 were blanks for background fluorescence (stop solution added before the enzyme). After substrate and inhibitor addition, the plates were prewarmed to 37° C. Incubations were initiated by the addition of prewarmed enzyme and cofactors. The enzymes were commercially available, baculovirus/insect cell expressed human CYP3A4 (SUPERSOMES®, Cat. no. P202, GENTEST Corporation) or CYP2C8 (SUPERSOMES®, Cat. no. P252, GENTEST Corporation). The amount of enzyme added per well was 0.2 pmoles (CYP3A4) or 4 pmoles (CYP2C8). The final cofactor concentrations were 1.3 mM NADP, 3.3 mM glucose-6-phosphate and 0.4 U/mL glucose-6-phosphate dehydrogenase. Final incubation volume was 0.2 ml. Incubations were carried out for 10 minutes (CYP3A4) or 30 min (CYP2C8) and stopped by the addition of 2 N sodium hydroxide solution. Fluorescence per well was measured using a BMG FLUOstar fluorescence plate reader controlled with an IBM-compatible computer. The metabolite was measured using an excitation wavelength of 485 nm and emission wavelength of 530 nm. Data was exported and analyzed using an Excel spreadsheet. The IC$_{50}$ values were calculated by linear interpolation.

Example 3

Specificity of Other Alkyl Fluorescein Compounds

The specificity of several cytochrome P450 enzymes for the dealkylation of two different commercially available alkyl ether fluoresceins was examined. 5-(and 6)-Chloromethylfluorescein diethyl ether (CMFDE, a mixture of isomers) is very similar to the diethoxyfluorescein studied by A. G. Miller (A. G. Miller, Anal. Biochem. 133, 46–57 (1983)). CMFDE must be dealklylated twice in order to form the fluorescent fluorescein product—5(and 6)-carboxyfluorescein. A. G. Miller reported that diethyl ethers of fluorescein are poor P450 substrates in mouse liver microsomes because they must be metabolized twice by the P450 enzyme in order to generate the fluorescent product. 3-O-Methylfluorescein (MF) is a simple, single methyl ether of fluorescein. The use of MF as a P450 substrate has never been reported.

Figure 4A:
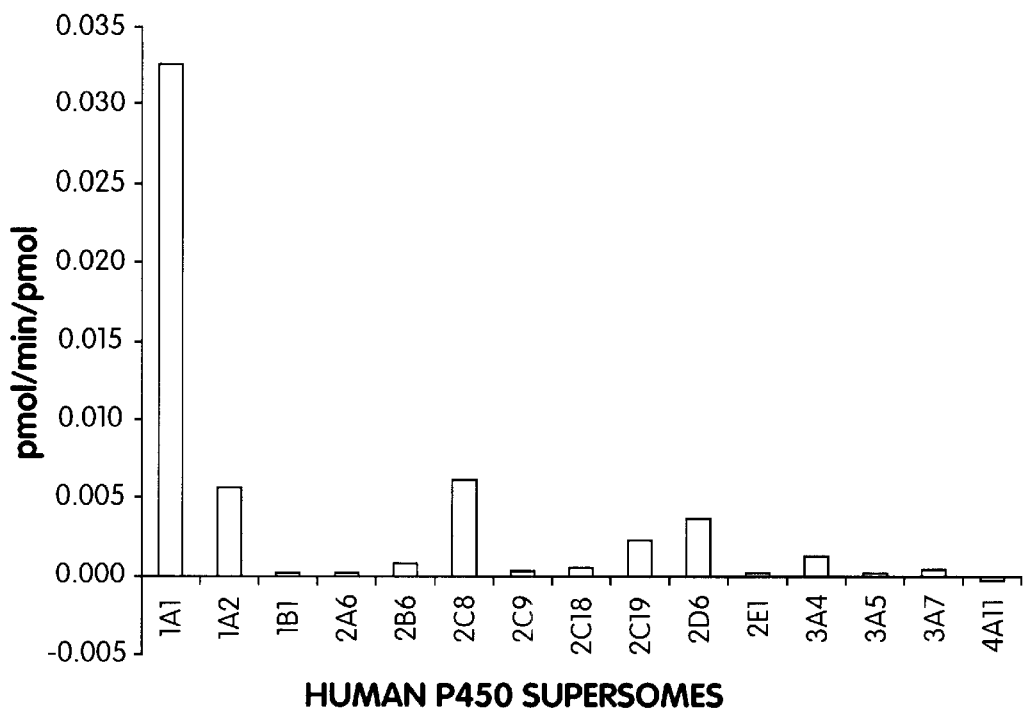
FIG. 4A shows selectivity for 5-(and-6)-chloromethylfluorescein diethyl ether (CMFDE) dealkylation by a panel of Human P450 Enzymes.
Figure 4B:
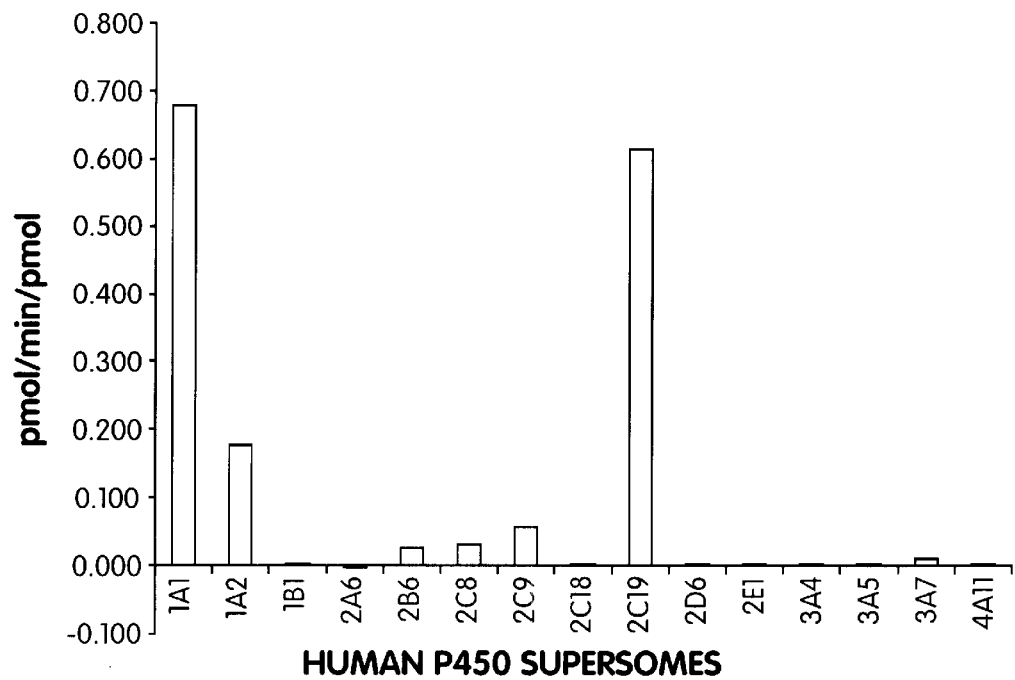
FIG. 4B shows selectivity for 3-O-methylfluorescein (MF) by a panel of Human P450 Enzymes.

The specificity for dealkylation of CMFDE by human cytochromes P450 is summarized in FIG. 4A. CMFDE is not a good substrate (based on turnover number) for any of the human P450 enzymes. CMFDE was a substrate for multiple P450 isoforms of drug metabolizing P450 enzymes showing little specificity except for CYP1A1. This metabolism profile is very different from that of other alkylfluoresceins (Compound Ia, Ib, and MF). The specificity for dealkylation of MF by human cytochromes P450 is summarized in FIG. 4B. MF is a good P450 substrate (based on turnover number) for CYP1A1 and CYP2C19. Since CYP1A1 is rare in human liver, this substrate may be very useful as a CYP2C19 specific probe in human liver tissue. Both of these examples illustrate the difficulty in predicting human P450 specificity for the dealkylation of alkylfluoresceins. The specificity profiles are very different from those of Compounds Ia and Ib.

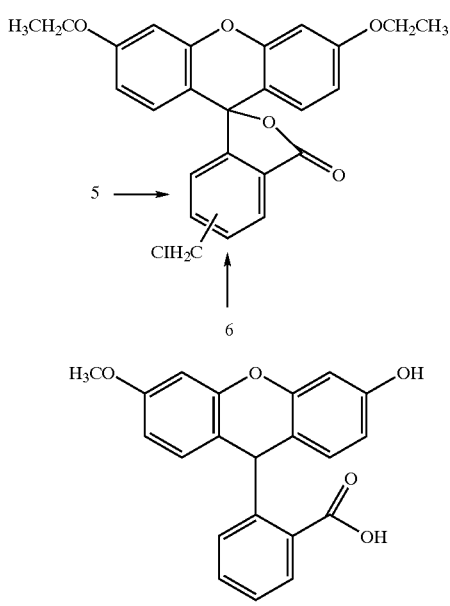

Examples CMFDE and MF. Assays were conducted in 96 well microtiter plates (Coming COSTAR, cat. no. 3915). The substrate, CMFDE or MF, was prepared in acetonitrile. After cofactors addition, the plates were prewarmed to 37° C. Incubations were initiated by the addition of prewarmed enzyme and substrate. The enzymes were commercially available, baculovirus/insect cell expressed human P450s (SUPERSOMES®, GENTEST Corporation). The amount of enzyme added per well was 2 pmole. The final substrate concentration was 1 uM, final cofactor concentrations were 1.3 mM NADP, 3.3 mM glucose-6-phosphate and 0.4 U/mL glucose-6-phosphate dehydrogenase. Final incubation volume was 0.2 ml. Incubations were carried out for 30 minutes and stopped by the addition of 0.075 mL of 2 N sodium hydroxide solution. Fluorescence per well was measured using a BMG FLUOstar fluorescence plate scanner equipped with an IBM-compatible computer. The metabolite was measured using an excitation wavelength of 485 nm and emission wavelength of 530 nm and compared to a standard curve of metabolite standard (5(and 6)-carboxyfluorescein for CMFDE and fluorescein for MF). Data was exported and analyzed using an Excel spreadsheet.

Example 4
Substrate Specificity with Rat P450s

Rats are a common in vivo animal model for human xenobiotic metabolism. There is much current interest in the species differences between rats and humans, especially in vitro models that would explain species differences or validate the rat as a good model for human xenobiotic metabolism. Few fluorescent assays have been developed for rat P450 enzymes. Most rat P450 assays are based on tedious HPLC assays. A quick and simple fluorescent plate-based assay would find utility in studying species differences in xenobiotic metabolism.

The specificity of several rat cytochrome P450 enzymes for the dealkylation of Compound Ia (FIG. 1) and other fluorescent cytochrome P450 substrates was examined. The data (turnover number) is summarized in Table V. Compound Ia was a substrate for multiple isoforms within the three major families of drug metabolizing P450 enzymes (as demonstrated by a high signal to noise ratio). The catalytic profiles for each substrate, including Compound Ia, are distinct. For those rat P450s that turnover Compound Ia, Compound Ia is the most sensitive assay reagent based on it's low limit of detection. This characteristic is likely due to the superior wavelength and quantum yield properties of the fluorescein product compared to the other coumarins and resorufin products. This data shows that Compound Ia is a promising fast and inexpensive substitute for many HPLC-based rat P450 assays.

Example Compound Ia. Assays were conducted in 96 well microtiter plates (Corning COSTAR, cat. no. 3915). The substrate, compound Ia, was prepared in acetonitrile. After cofactors addition, the plates were prewarmed to 37° C. Incubations were initiated by the addition of prewarmed enzyme and substrate. The enzymes were commercially available, baculovirus/insect cell expressed rat P450s (SUPERSOMES®, GENTEST Corporation). The amount of enzyme added per well was 2 pmole. The final cofactor concentrations were 1.3 mM NADP, 3.3 mM glucose-6-phosphate and 0.4 U/mL glucose-6-phosphate dehydrogenase. Final incubation volume was 0.2 ml. Incubations were carried out for 30 minutes and stopped by the addition of 0.075 mL of 2 N sodium hydroxide solution. Fluorescence per well was measured using a BMG FLUOstar fluorescence plate scanner equipped with an IBM-compatible computer. The metabolite was measured using an excitation wavelength of 485 nm and emission wavelength of 530 nm. Data was exported and analyzed using an Excel spreadsheet.

Example Other Fluorescent P450 Substrates. The substrate, buffer and protein concentrations and incubation times (see Table VI) were chosen based primarily on those conditions determined to be optimal for cytochrome P450 inhibition experiments for the human enzyme (e.g. CYP3A4 with BFC). This refers to a substrate concentration at or near the apparent Km and conditions of where metabolite production was linear with time and protein. Assay conditions were not necessarily optimal with all enzyme/substrate pairs, however, in most cases, substrate utilization was below 15%. A notable exception was CYP2D2/AMMC where substrate utilization was 45%. Therefore, the velocities reported were not necessarily measured under initial rate conditions.

TABLE VI

Turnover Numbers for Rat CYP Enzymes with Fluorometric Substrates[a]

| Rat CYP Isoform | Substrate | | | | | | |
|---|---|---|---|---|---|---|---|
| | Ia | AMMC | CEC | MFC | BFC | BQ | BzRes |
| CYP1A1 | 0.211 | —[b] | 78 | 1.03 | 0.34 | 5.7 | 1.35 |
| CYP1A2 | 0.041 | — | 1.38 | 1.32 | — | 2.3 | 0.62 |
| CYP2A1[c] | — | — | — | — | — | — | — |

TABLE VI-continued

Turnover Numbers for Rat CYP Enzymes with Fluorometric Substrates[a]

| | Substrate | | | | | | |
|---|---|---|---|---|---|---|---|
| Rat CYP Isoform | Ia | AMMC | CEC | MFC | BFC | BQ | BzRes |
| CYP2A2 | 0.030 | — | 0.04 | 0.08 | 0.26 | 2.8 | — |
| CYP2B1 | — | — | 0.45 | 2.82 | 3.70 | 2.5 | 0.82 |
| CYP2C6 | 0.021 | — | 2.14 | 11.5 | 2.62 | 1.9 | 0.02 |
| CYP2C11 | 0.065 | — | 0.55 | 5.57 | 0.34 | — | 0.05 |
| CYP2C12 | — | — | — | 0.24 | — | 1.5 | — |
| CYP2C13 | 0.003 | — | — | 0.21 | 0.74 | — | 0.01 |
| CYP2D1 | 0.159 | — | — | 0.09 | 0.25 | 5.3 | 0.02 |
| CYP2D2 | 0.194 | 5.9 | — | 0.08 | 0.12 | 4.4 | — |
| CYP2E1[c] | — | — | 0.10 | 2.11 | — | — | — |
| CYP3A1 | 0.027 | — | 0.08 | — | 1.33 | 8.4 | 0.06 |
| CYP3A2 | 0.015 | — | 0.15 | — | 1.04 | 9.8 | 0.09 |
| Substrate concentration (uM) | 2 | 20 | 40 | 50 | 50 | 40 | 50 |
| Incubation time (min) | 30 | 30 | 30 | 30 | 30 | 30 | 30 |
| Enzyme concentration (nM)[d] | 50 | 50 | 50[e] | 50 | 50 | 50 | 50 |

[a]Values, expressed as pmol product/min/pmol enzyme, represent the mean of duplicate determinations. Bold values indicate the highest catalytic activity within the panel.
[b]Dashes indicate activity was below the limit of detection which was considered as that corresponding to a signal to background ratio of approximately 1.5. These values and their substrates were
0.05 min$^{-1}$, AMMC;
0.05 min$^{-1}$, BFC;
0.008 min$^{-1}$, CEC;
0.003 min$^{-1}$, Ia;
0.05 min$^{-1}$, MFC;
1.0 min$^{-1}$, BQ;
0.008 min$^{-1}$, BzRes.
[c]Microsomes from human lymphoblastoid cells engineered to express the rat enzyme.
[d]Concentration for all enzymes was 50 nM except for CYP2A1 (20 nM) and for CYP2E1 (87 nM).
[e]Concentration for all enzymes was 50 nM except for CYP1A1, which was 2.5 nM.

The preceding is merely a detailed description of certain preferred embodiments. It therefore should be apparent to those skilled in the art that various modifications and equivalents can be made without departing from the spirit or scope of the invention.

All references disclosed herein are incorporated by reference in their entirety.

What is claimed is:

1. A method for assaying cytochrome P450 enzyme activity comprising:
   contacting a cytochrome P450 enzyme with a compound selected from the group consisting of:
   (a) a compound of Formula I;

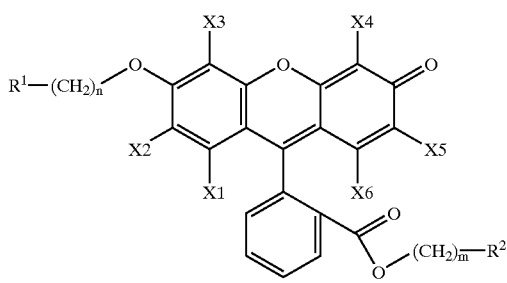

(1) wherein R1 is aryl and R2 is independently selected from the group consisting of an hydrido and an aryl, provided that R1 and R2 are not both phenyl when n and m are 1; and wherein the aryl contains an aryl ring carbon and/or an aryl ring nitrogen and the (CH$_2$)$_n$ or (CH$_2$)$_m$ is coupled via a covalent bond to the aryl ring carbon or the aryl ring nitrogen;
   (2) wherein n is 0, 1, 2, or 3;
   (3) wherein X1, X2, X3, X4, X5, and X6 are independently selected from the group consisting of an hydrido, a chloro, a fluoro, a bromo, and an iodo; and
   (4) wherein m is 0, 1, 2, or 3; and
   (5) wherein the compound is a cytochrome P450 substrate;
   (b) a compound of Formula III; and

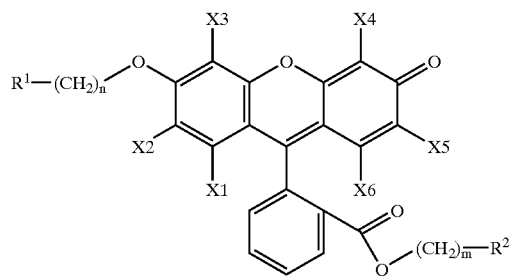

(1) wherein R1 and R2 are each phenyl; and wherein the phenyl contains an aryl ring carbon and the (CH$_2$)$_n$ or (CH2)$_m$ is coupled via a covalent bond to the aryl ring carbon;
   (2) wherein n is 1;
   (3) wherein X1, X2, X3, X4, X5, and X6 are independently selected from the group consisting of a chloro, a fluoro, a bromo, and an iodo;
   (4) wherein m is 1; and
   (5) wherein the compound is a cytochrome P450 substrate; and
   (c) benzyloxyfluorescein benzyl ester (DBF);
   under conditions whereby the cytochrome P450 enzyme catalyzes the conversion of the compound to a fluorescent product.

2. The method of claim 1, wherein the cytochrome P450 enzyme is contained in a biological sample.

3. The method of claim 1, wherein the sample is selected from the group consisting of a liver sample such as a crude homogenate, partially purified, or purified liver enzyme obtained from a biopsy, a cDNA-expressed cytochrome P450, hepatocytes, and microsomes.

4. The method of claim 1, wherein contacting is performed in the presence of a putative cytochrome P450 enzyme inhibitor, and under conditions whereby the cytochrome P450 enzyme catalyzes the conversion of the compound to a fluorescesnt product; said method further comprising the step of:

selecting an agent which inhibits cytochrome P450 enzyme activity as a cytochrome P450 enzyme inhibitor.

5. The method of claim 4, wherein the compound is contacted with the putative cytochrome P450 enzyme inhibitor in a multiwell plate well.

* * * * *